(12) United States Patent
Hudelist et al.

(10) Patent No.: US 10,092,484 B2
(45) Date of Patent: *Oct. 9, 2018

(54) COSMETIC COMPOSITION WITH INCREASED OPACITY

(71) Applicant: Conopco, Inc., Englewood Cliffs, NJ (US)

(72) Inventors: Florian Hudelist, Heidelberg (DE); Yajuan Li, Shanghai (CN); Zhaoting Liu, Shanghai (CN); Sheng Meng, Shanghai (CN); Qiang Qiu, Trumbull, CT (US); Lin Wang, Shanghai (CN); Xiaoli Wang, Shanghai (CN); Chunwei Wu, Temple City, CA (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/027,723

(22) PCT Filed: Sep. 30, 2014

(86) PCT No.: PCT/EP2014/070862

§ 371 (c)(1),
(2) Date: Apr. 7, 2016

(87) PCT Pub. No.: WO2015/055416

PCT Pub. Date: Apr. 23, 2015

(65) Prior Publication Data

US 2016/0235633 A1     Aug. 18, 2016

(30) Foreign Application Priority Data

Oct. 15, 2013  (CN) .................. PCT/CN2013/085249
Nov. 28, 2013  (EP) ..................................... 13194882

(51) Int. Cl.
| | |
|---|---|
| *A61K 8/02* | (2006.01) |
| *A61Q 19/08* | (2006.01) |
| *A61Q 19/00* | (2006.01) |
| *A61K 8/36* | (2006.01) |
| *A61K 8/29* | (2006.01) |
| *A61K 8/34* | (2006.01) |
| *A61K 8/73* | (2006.01) |
| *A61K 8/891* | (2006.01) |
| *A61K 8/37* | (2006.01) |
| *A61Q 17/04* | (2006.01) |
| *A61K 8/35* | (2006.01) |
| *A61Q 19/02* | (2006.01) |
| *A61K 8/49* | (2006.01) |
| *A61K 8/25* | (2006.01) |
| *A61K 8/81* | (2006.01) |
| *A61K 8/11* | (2006.01) |

(52) U.S. Cl.
CPC .............. *A61K 8/0245* (2013.01); *A61K 8/11* (2013.01); *A61K 8/25* (2013.01); *A61K 8/29* (2013.01); *A61K 8/342* (2013.01); *A61K 8/345* (2013.01); *A61K 8/35* (2013.01); *A61K 8/361* (2013.01); *A61K 8/37* (2013.01); *A61K 8/4926* (2013.01); *A61K 8/732* (2013.01); *A61K 8/8117* (2013.01); *A61K 8/891* (2013.01); *A61Q 17/04* (2013.01); *A61Q 19/00* (2013.01); *A61Q 19/007* (2013.01); *A61Q 19/02* (2013.01); *A61Q 19/08* (2013.01); *A61K 2800/26* (2013.01); *A61K 2800/412* (2013.01); *A61K 2800/43* (2013.01); *A61K 2800/621* (2013.01); *A61K 2800/652* (2013.01)

(58) Field of Classification Search
None
See application file for complete search history.

(56) References Cited

U.S. PATENT DOCUMENTS 7,758,888 B2   7/2010   Lapidot et al.

FOREIGN PATENT DOCUMENTS

| EP | 1206928 | | 9/2011 |
|---|---|---|---|
| EP | 1206928 B | * | 9/2011 |
| EP | 2500087 | | 9/2012 |
| WO | WO2004105712 | | 12/2004 |
| WO | WO2008079760 | | 7/2008 |
| WO | WO2011076518 | | 6/2011 |

OTHER PUBLICATIONS

IPRP in PCTEP2014071627, Jan. 11, 2016.
IRPR in PCTEP2014070862, Dec. 8, 2015.
Search Report & Written Opinion in EP13194880, dated Apr. 23, 2014.
Search Report & Written Opinion in PCTEP2014/070862, dated Feb. 2, 2016.
Search Report & Written Opinions in PCTEP2014071627, dated Feb. 3, 2015.
Written Opinion 2 in PCTEP2014070862, dated Sep. 8, 2015.
Co-Pending Application:Applicant:Hudelist et al.; Filed: Apr. 7, 2016, U.S. Appl. No. 15/027,716.
Bond et al., Optical Constants of ZnO (Zinc oxide), Refractive Index Database, 1965, pp. 1-2.
Hale and Querry, Optical constants of H2O D2O (water, heavy water, ice), Refractive Index Database H2O D2O water heavy water ice, 1973, pp. 1-2.
LD Didactic., Determination of the refractive index with the refractometer, Analytical Chemistry LD Chemistry Leaflets, 2015, pp. 1-4, C.3.3.3.1.
Janina Nowakowska, The refractive Indices of Ethyl Alcohol and Water Mixtures, Loyola ECommons Mater's Theses, 1939, pp. 1-55, Paper 668, Loyola University, Chicago.

(Continued)

*Primary Examiner* — Jianfeng Song
(74) *Attorney, Agent, or Firm* — Greenberg Traurig, LLP

(57) ABSTRACT

A cosmetic composition is disclosed comprising particle active and cosmetically acceptable carrier comprising hydrophobic material, wherein the hydrophobic material comprises less than 15% liquid oil by weight of the composition. The particle active comprises (i) water-insoluble shell component comprising inorganic material and having a refractive index of from 1.3 to 1.8; and (ii) core component comprising volatile liquid and having a refractive index of at least 1.2.

10 Claims, No Drawings

(56) References Cited

OTHER PUBLICATIONS

Elton et al., Application of Styrene/Acrylates Copolymer(SunSpheres in Cosmetic Systems; Research Disclosure; Dec. 1999; 1560;XP000934530; No. 42809.
Sunspheres Hollow Sphere Technology An SPF Booster for More Aesthetically Pleasing Formulations; Dow Personal Care; 2006; 1-14; XP055321502.
Micro Beads; Sunjin Internet Citation; 2005; 1-15; XP002546007; Ver. 1.9.

\* cited by examiner

COSMETIC COMPOSITION WITH INCREASED OPACITY

FIELD OF THE INVENTION

The present invention relates to cosmetic compositions. More particularly, the present invention relates to such compositions for topical application to skin wherein increased opacity is desired to provide benefits such as masking blemishes, evening skin tone and/or skin lightening.

BACKGROUND OF THE INVENTION

Cosmetic compositions of various kinds are widely used by consumers. Skin care cosmetics such as moisturizing lotions or creams are applied to obtain benefits of anti-aging, skin lightening and moisturizing, while make-up cosmetic products are applied to obtain desired optics and color benefits. Make-up cosmetics such as foundation and blemish-balm creams are able to deliver such covering and color benefits as a result of very high pigment and colorant content. Unfortunately, however, such high loadings can lead to an undesired feature of poor tactile sensory and for this reason moisturizers typically maintain low pigment dosage. It is the current trend that more and more make-up products are promoted to have moisturizer type in-use sensory and traditional moisturizers are formulated to deliver more perceivable optical benefits.

Whitening and opacifying optical properties delivered from moisturizer-type products generally come from their intrinsic emulsion structure (either W/O or O/W) and included particles with high refractive index, such as micronized titanium dioxide and zinc oxide. When topically-applied such products are usually spread to a very thin film (typically ~20 micron thickness) on the skin surface. This film is subject to a fast drying process during which emulsion droplets coalesce and break up and opacifying particles aggregate. As a consequence, the film loses most of its optical benefits within minutes after application. Thus, in order to compensate the time-dependent loss of optical benefits, a high level addition of the opacifying particles may be included in the formulation. However such heavy loadings typically bring unnatural whiteness on initial application and are therefore not an ideal technical solution.

The present inventors have thus recognized that there remains a need to provide cosmetic compositions that are capable of providing benefits, especially optical benefits, which are long lasting and/or actually increase with time after application. The present inventors have found that such a need may be met by providing particle actives with particular configuration and properties. In particular the inventors have found that particles with a shell formed from inorganic material having a specific refractive index and filled with a volatile material having a specific refractive index can meet such a need.

The application of inorganic core-shell particles in cosmetics has been described. In particular the use of such particles for encapsulating active materials has been described.

U.S. Pat. No. 7,758,888 (Sol-Gel Technologies Ltd.) discloses a therapeutic, cosmetic or cosmeceutic composition for topical application, capable of stabilizing an active ingredient and delivering the active ingredient, comprising a plurality of microcapsules having a core-shell structure. The microcapsules have a diameter of approximately 0.1 to 100 micron. The core of each microcapsule includes at least one active ingredient and is encapsulated within a microcapsular shell. The shell is comprised of at least one inorganic polymer obtained by a sol-gel process, and the shell protects the active ingredient before topical application and is designed to release the active ingredient from the microcapsules following application. The composition is said to be useful in encapsulating active ingredients, such as benzoyl peroxide, that are unstable in other formulation, or are irritating to the skin.

WO 2011/076518 A (EVONIK DEGUSSA GMBH) discloses a powdery composition comprising: a) at least one powder in form of core-shell particles, the core comprising liquid water or a liquid aqueous phase and the shell comprising hydrophobic or phobized particles and b) at least one powder comprising carrier and b1) at least partially water soluble liquid and/or b2) a water reactive substrate each located in and/or on the carrier. Provision of such compositions in a powdery form allows the particles to break upon application to the skin and so the particles are not in the form of core-shell particles after application.

The foregoing publications do not recognize the utility of particles with a shell having a certain refractive index and filled with a volatile material also having a certain refractive index in providing cosmetic compositions that are capable of providing optical benefits to the skin, especially which benefits are long lasting and/or actually increase with time after application. Furthermore the publications do not recognize the utility of applying such particles in cosmetic compositions comprising hydrophobic material but with relatively low contents of liquid oil.

DEFINITIONS

Refractive Index

Refractive index values referred to herein are those determined at a temperature of 25° C. and a wavelength of 589 nm unless otherwise stated.

Particle Size

Where the size of particles is mentioned (other than "primary particle size") this means the number average diameter determined, for example using scanning electron microscopy (SEM). Similarly "thickness" means the number average thickness determined, for example using scanning electron microscopy (SEM). In a preferred method, cryo-SEM is used to determine particle size and thickness. In cryo-SEM, a composition is quick-frozen in liquid nitrogen followed by cryo-planing to create a flat surface to be imaged. Typically the diameter and thickness are each averaged over at least 200 particles. For diameter determination, intact particles are selected from the SEM image whilst for shell thickness, particles which have been sectioned are selected.

In the event that a particle is not spherical then "diameter" means the largest distance measurable across the particle.

Where primary particle size is mentioned this means the size (diameter) measurable by transmission electron microscopy (TEM) using a method such as that described by S. Gu et al in *Journal of Colloid and Interface Science,* 289 (2005) pp. 419-426.

Hydrophobic Material

By "hydrophobic material" is meant a substance that is attracted to and tends to dissolve in a non-polar solvent (such as n-octanol) in preference to water at 25° C. and 1 atm. Preferred hydrophobic materials are insoluble in water. The term "liquid oil" as used herein refers to hydrophobic material with a melting point below 25° C. at 1 atm.

"Non-liquid hydrophobic material" refers to hydrophobic material other than liquid oil. Preferred hydrophobic materials are non-volatile.

Solubility "Soluble" and "insoluble", as used herein, refers to the solubility of a substance in a solvent (which, unless otherwise stated is water). Soluble means a substance that dissolves in the solvent to give a solution with a concentration of at least 1 g per liter at room temperature (25° C.) and pressure (1 atm). Insoluble means a substance that dissolves in the solvent to give a solution with a concentration of less than 1 g per liter at room temperature and pressure.

Volatility

The term "volatile" as used herein refers to a substance which has a vapour pressure of at least 1000 Pa at 25° C. and a non-volatile substance is one wherein the vapour pressure is less than 1000 Pa.

Leave-on and Wash-off

The term "leave-on" as used with reference to compositions herein means a composition that is applied to or rubbed on the skin, and left thereon. The term "wash-off" as used with reference to compositions herein means a skin cleanser that is applied to or rubbed on the skin and rinsed off substantially immediately subsequent to application.

Skin

The term "skin" as used herein includes the skin on the face (except eye lids and lips), neck, chest, abdomen, back, arms, hands, and legs. Preferably "skin" means skin on the face.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final composition, unless otherwise specified.

The term "solid" as used herein means that the material is not fluid at 25 degrees C.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to a cosmetic composition in the form of a paste, gel, liquid or monolithic solid and comprising:
(a) particle active, wherein the particle active comprises:
 (i) water-insoluble shell component comprising inorganic material and having a refractive index ($n_s$) of from 1.3 to 1.8; and
 (ii) core component comprising volatile liquid and having a refractive index ($n_c$) of at least 1.2, wherein the core component comprises at least 75% water by weight of the core component; and
(b) cosmetically acceptable carrier comprising hydrophobic material, wherein the hydrophobic material comprises less than 15% liquid oil by weight of the composition.

In a second aspect the invention is directed to a process for making any embodiment of the composition of the first aspect, the process comprising: combining the particle active with the carrier; and recovering the composition.

In a third aspect the present invention provides a method for improving one or more skin characteristics comprising the steps of:
I. providing a composition according to any embodiment of the first aspect;
II. topically applying the composition to skin; and
III. allowing the volatile liquid to evaporate from the particle active.

In a fourth aspect the invention provides use of a particle active for providing a skin benefit selected from masking blemishes, evening skin tone, skin lightening or a combination thereof, wherein the particle active comprises:
(i) water-insoluble shell component comprising inorganic material and having a refractive index ($n_s$) of from 1.3 to 1.8; and
(ii) core component comprising volatile liquid and having a refractive index ($n_c$) of at least 1.2.

Preferably the particle active is as described in any embodiment of the first aspect of the invention.

In a fifth aspect the invention provides use of the composition of any embodiment of the first aspect for providing a skin benefit selected from masking blemishes, evening skin tone, skin lightening or a combination thereof.

All other aspects of the present invention will more readily become apparent upon considering the detailed description and examples which follow.

DETAILED DESCRIPTION

The only limitation with respect to the type of particle active that may be used in this invention is that the same can be employed in a cosmetic composition suitable for topical application to skin, and that the particle active comprises:
(i) water-insoluble shell component comprising inorganic material and having a refractive index ($n_s$) of from 1.3 to 1.8; and
(ii) core component comprising volatile liquid and having a refractive index ($n_c$) of at least 1.2.

Without wishing to be bound by theory, the present inventors believe that as the volatile liquid evaporates from the particle core (e.g. after application to skin), it is replaced by air. Air has a relatively low refractive index and so a mismatch (or at least an increased mismatch) in refractive index between the core and the shell of the particle active develops. This in turn means that the light scattering efficiency of the particles increases and the overall optical benefits provided by the composition evolve with time after application.

The shell component is water-insoluble but is preferably permeable to water. At least the shell should be permeable sufficient to allow the volatile liquid to evaporate from the core when the particle active is exposed to air at 25° C. and 1 atm. Most preferably the shell component is permeable sufficient to allow substantially all of the volatile liquid (e.g. 90-100% by weight of the total volatile liquid in the core) to evaporate from the core when the particle active is exposed to air at 25° C. and 1 atm for 12 hours, or even 6 or 3 hours.

Typically the shell component will be solid.

The shell component comprises an inorganic material. A most preferred inorganic material for the shell component is inorganic polymer, especially inorganic polymer obtained by a sol-gel process as such polymers can be formed into shell-like particles using methods such as those described for example in U.S. Pat. No. 7,758,888, the disclosure of which is hereby incorporated by reference in its entirety (but especially column 13 [lines 15-39] thereof). Inorganic polymer is preferably formed from pure silica, organically-modified silica, or a combination thereof, most preferably from silica.

The shell component may comprise organic material in addition to inorganic material but in a preferred embodiment the shell component comprises at least 80% inorganic material by weight of the shell component, more preferably at least 90% and most preferably from 95 to 100%. In an especially preferred embodiment the shell consists (or at least consists essentially) of inorganic material, most especially silica.

The refractive index of the shell component should be sufficiently larger than the refractive index of air such that once the volatile liquid evaporates from the core of the particle active, the air which replaces it has a significant refractive index mismatch with the shell. Thus the water-insoluble shell component has a refractive index ($n_s$) of at least 1.3, more preferably at least 1.4. The refractive index is not too high, however, otherwise the shell may have a significant refractive index mismatch with the volatile liquid. Thus $n_s$ is no greater than 1.8, preferably less than 1.7, more preferably less than 1.6 and most preferably less than 1.5.

The core component comprises volatile liquid and preferably consists essentially of, or even consists of volatile liquid. The liquid is volatile such that it may evaporate from the core when the particle active is exposed to air at 25° C. and 1 atm. Preferably the volatile liquid has a vapour pressure of at least 2000 Pa at 25° C. most preferably at least 2.5 kPa. The liquid need not be too volatile, however, otherwise it may prematurely escape from the particle active. Preferably the volatile liquid has a vapour pressure of less than 50 kPa at 25° C. more preferably less than 15 kPa. Preferred volatile liquids include volatile silicones, C1-C5 alcohols, water or a mixture thereof. Most preferred is water. Preferably the core component comprises at least 50% water by weight of the core component, more preferably at least 75%, more preferably still at least 85% and most preferably from 90 to 100%.

The refractive index of the core component should be sufficiently larger than the refractive index of air such that a refractive index mismatch develops or at least increases when the liquid is replaced by air. Thus the core component has a refractive index ($n_c$) of at least 1.2, more preferably at least 1.25 and most preferably at least 1.3. The refractive index need not be too high and $n_c$ may, for example, be less than 2.0, more preferably less than 1.8, more preferably still less than 1.5, even more preferably less than 1.45 and most preferably less than 1.4.

In a most preferred embodiment the refractive indices of the shell and core are substantially matched such that a mismatch develops only when the volatile liquid evaporates from the core. For example, the ratio of the refractive index of the core to the refractive index of the shell ($n_c/n_s$) is preferably from 0.7 to 1.2, more preferably from 0.8 to 1.1, most preferably from 0.85 to 1.0.

Light scattering properties of the particle active are enhanced if the particles are micronized. Thus it is preferred that the particle active has a particle size (D) of no greater than 50 microns, more preferably less than 20 microns, more preferably still less than 10 microns, even more preferably less than 5 microns and most preferably less than 2 microns.

It has been found, however that the particles need not be too small and effective optical effects can be obtained with relatively large particles. Thus it is preferred that the particle active has a particle size (D) of at least 200 nm, more preferably at least 500 nm, more preferably still at least 600 nm, even more preferably at least 700 nm and most preferably at least 800 nm.

It has also been found that particle actives with relatively thick shells give especially good optical effects. Thus in a preferred embodiment the relationship between the thickness (L) of the shell component and the size (D) of the particle active follows equation (I):

$$L \cdot 150\ \text{nm} - 0.25 \times D \quad \text{(I).}$$

The particle active is preferably spherical or spheroidal, most preferably spherical.

Preferably each particle of the particle active comprises (more preferably consists essentially of or consists of) a single core component encapsulated by the shell component.

The cosmetic composition preferably comprises the particle active in amount of from 0.001 to 20% shell component by weight of the composition, more preferably from 0.01 to 10%, more preferably still from 0.1 to 6%, even more preferably from 0.2 to 4%, and most preferably from 0.5 to 2.5%.

The composition of the present invention preferably comprises opacifying particles. These are particles with very high refractive index, i.e., having a refractive index of at least 1.7. For example the opacifying particles may have a refractive index of greater than 1.8, more preferably greater than 1.9 and most preferably from 2.0 to 2.7. Examples of such opacifying particles are those comprising bismuth oxy-chloride, boron nitride, titanium dioxide, zirconium oxide, aluminium oxide, zinc oxide or combinations thereof. More preferred are opacifying particles comprising zinc oxide, zirconium oxide, titanium dioxide or a combination thereof as these materials have especially high refractive index. Most preferred are opacifying particles comprising titanium dioxide. Preferably the composition comprises opacifying particles in an amount of from 0.001 to 10 wt %, more preferably 0.01 to 7 wt %, more preferably still 0.02 to 5 wt % and most preferably 0.05 to 2 wt %, wherein amount of particle active is in terms of weight of shell component by weight of the composition.

Opacifying particles are preferably micronized. Preferably the opacifying particles have a primary particle size in the range of from 20 to 2000 nm, and more preferably from 25 to 900 nm, and most preferably, from 30 to 400 nm, including all ranges subsumed therein.

The opacifying particles are typically separate from the particle active (i.e., the composition comprises particle active and additionally comprises the opacifying particles). Owing to their greater opacifying ability, the opacifying particles are typically compounded in the composition at a lower level than the particle active. For example, the composition preferably comprises the particle active and opacifying particles in a weight ratio (particle active : opacifying particles) of from 1000:1 to 1:1, more preferably 100:1 to 1.5:1, more preferably still from 50:1 to 2:1 and most preferably from 20:1 to 3:1, wherein amount of particle active is in terms of weight of shell component.

The present inventors have also found that inclusion of yellow pigment in the composition can help provide appearance benefits to skin. In particular it is found that the opacity afforded to skin by the particle active and opacifying particles (when present) can occasionally appear in uneven "patches" even when the composition is applied evenly and that the presence of yellow pigment can ameliorate this effect. Thus in a preferred embodiment the composition comprises yellow pigment.

The yellow pigment is preferably present in an amount in the range of 0.001 to 3 percent by weight of the composition, more preferably from 0.01 to 2.5%, more preferably still from 0.05 to 2%, and most preferably from 0.1 to 1.5%. The yellow pigment is preferably a metal oxide. Suitable metal oxides include titanium dioxide, iron oxide, or stannous oxide. Alternately the yellow pigment is of organic origin. Commercially available yellow pigments which may be used in the formulation include BGYO-TTB2 (from Kobo Product Inc, USA), SI2 Yellow LLXLO (from Daito Kasei Kogyo Company, Japan), Bronze 43737 (from Sudarshan Chemicals, India), Tatrazine Yellow (from Davarson, India), turmeric extract or a mixture thereof. Most preferred is iron oxide with the Colour Index Constitution Number (C.I.) 77492.

The preferred metal oxide is yellow iron oxide. The iron oxide is preferably suitably coated or encapsulated to minimize interactions with other ingredients of the composition. For example, when organic sunscreens are present in the formulation e.g. butylmethoxydibenzoylmethane sold as Parsol 1789 (Givaudan), they interact with iron oxide and produce an undesirable red colour. To minimize such interaction, the metal oxide particles are preferably coated with materials like mica and/or silicones (e.g. methyl hydrogen polysiloxanes, more preferably silicones). An example of a coated yellow iron oxide is the aforementioned BGYO-TTB2 which has I.N.C.I Name: Iron Oxides (C.I. 77492) (And) Isopropyl Titanium Triisostearate (And) Triethoxysilylethyl Polydimethylsiloxyethyl Dimethicone.

In a preferred embodiment the composition may additionally or alternatively comprise red pigment, black pigment or a combination thereof. More preferred is red pigment in combination with the yellow pigment, even more preferably the composition comprises yellow pigment, red pigment and black pigment. The total amount of pigment in the composition is preferably in the range 0.001 to 4 percent by weight of the composition, more preferably from 0.01 to 3%, more preferably still from 0.05 to 2.5%, and most preferably from 0.1 to 2%.

Compositions of the present invention will also include a cosmetically acceptable carrier. The carrier comprises hydrophobic material, wherein the hydrophobic material comprises less than 15% liquid oil by weight of the composition. The inventors have found that contact of the particle active with large amounts of liquid oil can impair the optical benefits afforded by the particle active. Preferably the hydrophobic material comprises less than 12% liquid oil by weight of the composition, more preferably still less than 10%, even more preferably less than 8% and most preferably from 0.01 to 5%.

In some embodiments the carrier will be (or at least comprise) a water and oil emulsion, which in certain embodiments may be water-in-oil emulsion. Preferred emulsions, however, are the oil-in-water variety. Where the carrier is an emulsion, it is preferred that the particle active is dispersed in the aqueous phase of the water and oil emulsion to minimize interaction of the particle active with any liquid oil in the composition.

Regardless of the amount of liquid oil in the composition, the hydrophobic material may comprise non-liquid hydrophobic material. In particular the composition may contain non-liquid hydrophobic material in an amount of from 0.01 to 80% by weight of the composition, more preferably from 0.1 to 30%, more preferably still from 0.5 to 25% and most preferably from 1 to 10%.

Preferred hydrophobic material for use in the present invention includes emollients such as fats, oils, fatty alcohols, fatty acids, soaps, silicone oils, synthetic esters and/or hydrocarbons. Many organic sunscreens are also hydrophobic materials and may be used alone or in combination with one or more of the foregoing emollients.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Nonvolatile silicones useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m²/s at 25° C. Among the preferred nonvolatile emollients useful in the present compositions are the polydimethyl siloxanes having viscosities from about $1 \times 10^{-8}$ to about $4 \times 10^{-4}$ m²/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44).

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:
a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oleyl myristate, oleyl stearate, and oleyl oleate;
b) Ether-esters such as fatty acid esters of ethoxylated fatty alcohols;
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol monoand di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate;

d) Wax esters such as beeswax, spermaceti wax and tribehenin wax;

e) Sterols esters, of which cholesterol fatty acid esters are examples thereof;

f) Sugar ester of fatty acids such as sucrose polybehenate and sucrose polycottonseedate; or g) mixtures of two or more of the foregoing (a) to (f).

Of particular use also are the $C_{12-15}$ alkyl benzoate esters sold under the Finsolve brand.

Hydrocarbons which are suitable emollients include petrolatum, mineral oil, $C_{11}$-$C_{13}$ isoparaffins, polyalphaolefins, isohexadecane or a mixture thereof.

In a particularly preferred embodiment, the hydrophobic material comprises 1 to 25% fatty acid or 0.1 to 80% soap by weight of the composition. Mixtures of fatty acid and soap are also suitable e.g. vanishing cream base which gives a highly appreciated matty feel to the skin. C12 to C20 fatty acids are especially preferred for the present invention, more preferred being C14 to C18 fatty acids. The most preferred fatty acid is stearic acid, myristic acid or a mixture thereof. The fatty acid in the composition is more preferably present in an amount in the range of 5 to 20% by weight of the composition. Soaps in the hydrophobic material can include alkali metal salt of fatty acids, like sodium or potassium salts, most preferred being potassium stearate. The soap in the hydrophobic material is generally present in an amount in the range of 0.1 to 10%, more preferably 0.5 to 3% by weight of the composition. Generally a vanishing cream base in cosmetic compositions is prepared by taking a desired amount of total fatty matter and mixing with potassium hydroxide in desired amounts. The soap is usually formed in-situ during the mixing.

The carrier preferably comprises water. Amounts of water may, for example, range from 1 to 99%, more preferably from 5 to 90%, even more preferably from 35 to 80%, optimally between 40 and 70% by weight of the cosmetic composition.

The composition of the invention preferably comprises a skin lightening agent. The skin lightening agent is preferably chosen from one or more of a vitamin B3 compound or its derivative e.g. niacin, nicotinic acid or niacinamide or other well known skin lightening agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), morus alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition preferably additionally comprises one or more organic sunscreens. A wide variety of organic sunscreen agents are suitable for use in combination with the essential ingredients of this invention. Suitable UV-A/UV-B sunscreen agents include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen agent.

Other materials which can be included in the cosmetically acceptable carrier include solvents, humectants, thickeners and powders. Examples of each of these types of material, which can be used singly or as mixtures, are as follows:

Solvents include ethyl alcohol, isopropanol, acetone, ethylene glycol monoethyl ether, diethylene glycol monobutyl ether, diethylene glycol monoethyl ether and mixtures thereof.

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Powders include chalk, talc, Fullers earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The compositions of the present invention are not in a powdery form as it is desirable that the particle active is not broken on application to skin. Without wishing to be bound by theory, the present inventors believe that the presence of the particle active in core-shell form on the skin provides the advantageous optical effects of the invention. The compositions are thus in the form of a paste, gel, liquid or monolithic solid (e.g. a soap bar). Preferred formats are creams or lotions.

The cosmetic composition of this invention is a composition suitable for topical application to human skin, including leave-on and wash-off products. Preferably the term encompasses a fluid liquid, and particularly a moisturizer rather than a make-up product. Most preferred are leave-on compositions.

Packaging for the composition of this invention can be a jar or tube as well as any other format typically seen for cosmetic, cream, washing and lotion type products. The compositions may be applied topically and preferably 1-4 milligrams of composition is applied per square centimeter of skin.

The following examples are provided to facilitate an understanding of the invention. The examples are not intended to limit the scope of the claims.

EXAMPLES

Example 1

This example demonstrates the manufacture of core-shell particles useful for the invention and wherein the shell is formed from sol-gel polymerized inorganic polymer.
Materials
Styrene (St) was purchased from Sinopharm Chemical Reagent Co. (China) and purified by treating with 5 wt % aqueous NaOH to remove the inhibitor. An MTC [2-(methacryloyl)-ethyltrimethylammonium chloride] (80 wt %) aqueous solution was supplied by SIGMA-ALDRICH, Co. (USA). 2,2'-Azoisobutyronitrile (AIBN, 98%, Aldrich USA) was re-crystallized from tetrahydrofuran (THF) before use. a,a'-azodiisobutyramidine dihydrochloride(AIBA), ploy(vinyl pyrrolidone) (PVP, K30, Mw=30 000), TEOS (triethylorthosilicate), absolute ethanol, and aqueous ammonia solution (28 wt %) were purchased from Sinopharm Chemical Reagent Co.(China) and used as received. Deionized water was applied for all polymerization and treatment processes.
Synthesis of PS Templates
Polystyrene particles with particle size above 1·m were synthesized by dispersion polymerization. In a typical procedure, positively charged PS particles with a diameter of 1500 nm were synthesized as follows: 10.0 g of St, 3.0 g of PVP, 0.35 g of AIBN, 40.0 g of ethanol, 10.0 g of $H_2O$ were mixed in a 500 ml three-necked flask equipped with a mechanical stirrer, thermometer with a temperature controller, an $N_2$ inlet, a Graham condenser, and a heating mantle. The mixing solution was first deoxygenated by bubbling nitrogen gas at room temperature for 30 min, and then heated to 70° C. with a stirring rate of 180 rpm for 1.5 h, followed by addition of a mixture of 10.0 g St, 40.0 g of ethanol and 0.78 g of MTC.

Table 1 summarizes recipes for the synthesis of different sized PS template spheres (St 20 g, PVP 3.0 g, AIBN 0.35 g).

TABLE 1

| $H_2O$ (g) | EtOH (g) | EtOH(g)/$H_2O$ (g) | Particle size (nm) |
|---|---|---|---|
| 15 | 75 | 1:5 | 1000 |
| 10 | 80 | 1:8 | 1500 |
| 7 | 83 | 1:11.8 | 1800 |

Synthesis of $SiO_2$ Hollow Spheres
In a typical run, 5.5 ml of ammonia was added to the above-obtained dispersion and the mixture was stirred at 180 rpm for 5 min. 15 g of TEOS was added quickly and the mixture was maintained at 50° C. for around 1 h under constant stirring. The obtained spheres were separated from the reaction solution by centrifuging at 10000 rpm for 7 min. PS/$SiO_2$ hybrid particles were dried at 80° C. overnight to yield dried powders. The calcinations step used for removing PS core template was performed as the follows: the products were heated from room temperature to 550° C. at a heating rate of 1° C./min in the air atmosphere and then kept at 550° C. for another 2 h. Finally, the products were cooled down to room temperature in the air.

SEM images of the $SiO_2$ hollow spheres obtained with different diameters showed that their diameters roughly equated with the diameters of the PS templates (i.e., 1000 nm, 1500 nm or 1800 nm) and that the shell of each particle had a thickness of around 20 nm.

Example 2

Example formulations of two cosmetic compositions in the form of vanishing creams according to the invention are given in Table 2.

TABLE 2

| Ingredient (% w/w) | Vanishing Cream 1 | Vanishing Cream 2 |
|---|---|---|
| Stearic Acid | 17 | 5 |
| Myristic Acid | — | 5 |
| Niacinamide | 1.25 | 3 |
| Glycerine | 5 | 1 |
| Propylene glycol | 10 | — |
| Neutralizing Agent (Base) | 0.48 | 0.66 |
| Carbomer | — | 0.2 |
| Tapioca Starch | — | 0.7 |
| Cetyl Alcohol | 0.53 | 0.53 |
| Dimethicone | 0.5 | 0.563 |
| Isopropyl myristate | 1 | — |

TABLE 2-continued

| Ingredient (% w/w) | Vanishing Cream 1 | Vanishing Cream 2 |
|---|---|---|
| Methyl/propyl paraben | 0.3 | 0.3 |
| Parsol MCX (Ethylhexyl Methoxycinnamate) | 0.75 | 1.25 |
| Parsol 1789 (Butylmethoxy Dibenzoyl Methane) | 0.4 | 0.4 |
| Titanium Dioxide (80 nm)[1] | 1 | 0.8 |
| Titanium Dioxide (400 nm)[2] | 2 | — |
| Pigment | 1.29[3] | 0.015[4] |
| Core-Shell Particles | 2 | 2 |
| Minors[5] | 1.37 | 0.86 |
| Water | To 100 | To 100 |

[1]MT700Z = Titanium Dioxide (and) Stearic Acid (and) Aluminium Hydroxide supplied by TAYCA - size in brackets is primary particle size
[2]SA-TR-10 = Titanium Dioxide (and) Dimethylpolysiloxane supplied by Miyoshi Kasei Inc. - size in brackets is primary particle size.
[3]Mixture of Yellow, Red and Black Pigments.
[4]Red Pigment.
[5]Minors include vitamins, perfumes, sequestrants, bacteriacides and other skin benefit agents.

The core-shell particles used in these formulations were the SiO$_2$ hollow spheres of Example 1.

Example 3

An example formulation of a cosmetic composition in the form of a moisturizer according to the invention is given in Table 3.

TABLE 3

| Ingredient (% w/w) | Moisturizer |
|---|---|
| Stearic Acid | 3 |
| Niacinamide | 3 |
| Glycerine | 1 |
| Neutralizing Agent (Base) | 1.05 |
| Carbomer | 0.4 |
| Cetyl Alcohol | 0.5 |
| Mineral Oil | 1.5 |
| Glyceryl Monostearate | 1.5 |
| Dimethicone (200 cSt) | 0.5 |
| Isopropyl Myristate | 2 |
| Methyl/Propyl Paraben | 0.3 |
| Parsol MCX (Ethylhexyl Methoxycinnamate) | 1.25 |
| Parsol 1789 (Butylmethoxy Dibenzoyl Methane) | 0.4 |
| Titanium Dioxide (80 nm)[1] | 0.6 |
| Titanium Dioxide (400 nm)[2] | 0.2 |
| Pigment[3] | 0.068 |
| Core-Shell Particles[4] | 1.5 |
| Minors[5] | 1.211 |
| Water | To 100 |

[1]MT700Z.
[2]SA-TR-10.
[3]Mixture of Yellow and Red Pigment.
[4]Prepared as in Example 1.
[5]Minors include vitamins, perfumes, sequestrants, bacteriacides and other skin benefit agents.

The liquid oil in this composition includes mineral oil, dimethicone, isopropyl myristate, ethylhexyl methoxycinnamate and phenoxyethanol. The total amount of liquid oil is 5.7% by weight of the composition.

Example 4

This example demonstrates the effect of various particles on long lasting opacity in a moisturizer base.

Three samples were prepared using the moisturizer base described in Example 3 but with different amounts and/or types of opacifying particles and/or core-shell particles as shown in Table 4. These samples did not contain any red or yellow pigment.

TABLE 4

| Ingredient (% w/w) | Sample 1 | Sample 2 | Sample 3 |
|---|---|---|---|
| Titanium Dioxide (80 nm) | — | 2.0 | — |
| Titanium Dioxide (400 nm) | — | — | — |
| SiO$_2$ Hollow Sphere[1] (1.5 μm) | — | — | 1.75 |

[1]Prepared as described in Example 1—amount is in terms of SiO$_2$.

Opacity was measured using a Minolta™ CM2600D Spectrometer in SCE mode during controlled drying (23° C. 45% RH) of applied film. For each sample, a film was applied on a black/white draw-down card using a cubic film applicator of 75 microns.

Reflectance values of the film at various times after application were measured on both white and black backgrounds. The opacity was calculated as the ratio of the reflectance on black/white background at the wavelength of 450 nm. Table 5 shows the change in opacity for each sample film over 60 minutes (i.e., Opacity Change=opacity at 60 minutes–opacity at 0 minutes).

TABLE 5

| Sample | Change in Opacity after 60 min |
|---|---|
| 1 | 0.007 |
| 2 | −0.077 |
| 3 | 0.195 |

These results demonstrate that the sample containing core-shell particles (Sample 3) showed the ability to increase opacity with time after application.

Example 5

This example demonstrates the effect of opacifying particles and core-shell particles on long lasting skin lightening in a moisturizer base.

Two samples were prepared using the moisturizer base described in Example 3 but with different amounts of opacifying particles and/or core-shell particles (1 micron SiO$_2$ spheres from Example 1) as shown in Table 6. These samples did not contain any red or yellow pigment.

TABLE 6

| Ingredient (% w/w) | Sample 1 | Sample 2 |
|---|---|---|
| Titanium Dioxide (80 nm) | — | 0.6 |
| Titanium Dioxide (400 nm) | — | — |
| Core-Shell Particles[1] | 2.0 | 2.0 |

[1]Amount is in terms of SiO$_2$.

Opacity was measured using a Minolta™ CM2600D Spectrometer in SCE mode during controlled drying (23° C., 45% RH) of applied film. For each sample, a film was applied on a black/white draw-down card using a cubic film applicator of 75 microns.

Reflectance values of the film at various times after application were measured on both white and black backgrounds. The opacity was calculated as the ratio of the reflectance on black/white background at the wavelength of 450 nm. Table 7 shows the opacity for each sample film over 60 minutes after application.

TABLE 7

| Time (min) | • Sample 1 | • Sample 2 |
| --- | --- | --- |
| 0 | 0.06 | 0.16 |
| 5 | 0.06 | 0.15 |
| 10 | 0.12 | 0.11 |
| 15 | 0.18 | 0.17 |
| 20 | 0.27 | 0.20 |
| 30 | 0.30 | 0.26 |
| 60 | 0.34 | 0.32 |

The data in Table 7 demonstrates that presence of opacifying particles (Sample 2) provides immediate opacity (i.e., opacity at 0 min) to the greatest extent. However both samples showed an increase in opacity with time. The use of core-shell particles in both samples resulted in opacity which remarkably increased during 60 minutes to a value higher even than that of the immediate lightness produced by the opacifying particles. However, the sample containing both opacifying and core-shell particles (Sample 2) showed the best balance of both immediate and long-lasting opacity.

Example 6

This example demonstrates the effect of liquid oil content on the ability of core-shell particles to provide long lasting opacity.

Two moisturizer bases were used without pigments and opacifying particles. The first base is that used in the moisturizer of Example 3 ("low liq. oil base"). The second base had a liquid oil content of over 17 wt % ("high liq. oil base"). Core-shell particles (1.5 μm $SiO_2$ particles of Example 1) were added to each base in an amount of 1.75% $SiO_2$ by weight of the final moisturizer composition.

Opacity was measured using a Minolta™ CM2600D Spectrometer in SCE mode during controlled drying (23° C., 45% RH) of applied film. For each sample, a film was applied on a black/white draw-down card using a cubic film applicator of 75 microns.

Reflectance values of the film at various times after application were measured on both white and black backgrounds. The opacity was calculated as the ratio of the reflectance on black/white background at the wavelength of 450 nm. Table 8 shows the opacity for each sample film over 60 minutes after application.

TABLE 8

| Time (min) | • Low liq. oil base | High liq. Oil base |
| --- | --- | --- |
| 0 | 0.06 | 0.24 |
| 5 | 0.07 | 0.08 |
| 15 | 0.24 | 0.05 |
| 30 | 0.24 | 0.05 |
| 60 | 0.26 | 0.05 |

The data in table 8 demonstrates that the core-shell particles are able to increase opacity after 60 minutes for the low liquid oil base. In contrast in the high liquid oil base the hollow spheres were unable to prevent the opacity decreasing over 60 minutes after application.

Cryo-SEM images of the samples showed that, in contrast to the low-liquid oil base, the core-shell particles in the high liquid oil base appeared to be covered by and entrapped by oily material. Without wishing to be bound by theory the present inventors postulate that this covering may prevent or at least inhibit water from evaporating from the particles as the film dries. Alternatively the coating of liquid oil may reduce the refractive index contrast between the shell and the surrounding medium such that scattering efficiency is reduced.

The invention claimed is:

1. A cosmetic composition having increased opacity comprising:
   a. particle active, wherein the particle active comprises:
      i. water-insoluble shell component comprising inorganic material and having a refractive index ($n_s$) of from 1.3 to 1.8 at 25 degrees Celsius and a wavelength of 589 nm;
      ii. core component comprising volatile liquid and having a refractive index ($n_c$) of at least 1.2 at 25 degrees Celsius and a wavelength of 589 nm, wherein the core component comprises at least 75% water by weight of the core component; and
      iii. wherein the particle active has a particle size (D) of at least 500 nm and less than 1800 nm;
   b. cosmetically acceptable carrier comprising hydrophobic material, wherein the hydrophobic material comprises less than 15% liquid oil by weight of the cosmetic composition;
      wherein the cosmetic composition comprises 0.001 to 3 wt % yellow pigment;
      wherein the water insoluble shell component is from 0.5% to 2.5% of the cosmetic composition;
      wherein the hydrophobic material comprises:
         i) at least one liquid oil in an amount of from 0.01 to 10% by weight of the cosmetic composition,
         ii) at least one fatty acid in an amount of 1 to 25% by weight of the cosmetic composition, and
         iii) at least one soap in an amount of 0.1 to 10% by weight of the cosmetic composition; and
      wherein the cosmetic composition is configured to be applied to skin in the form of a paste, gel, liquid or a monolithic solid;
   c. opacifying particles wherein a weight ratio of the particle active to the opacifying particles is from 20:1 to 2:1.

2. The cosmetic composition as claimed in claim 1 wherein the cosmetic composition is a cream or lotion.

3. The cosmetic composition as claimed in claim 1 wherein the inorganic material is inorganic polymer, selected from the group consisting of: silica, organically-modified silica, and a combination thereof.

4. The cosmetic composition as claimed in claim 3 wherein the inorganic polymer is obtained by a sol-gel process.

5. The cosmetic composition as claimed in claim 1 wherein the shell is permeable to water.

6. The cosmetic composition as claimed in claim 1 wherein the ratio of the refractive index of the core to the refractive index of the shell ($n_c/n_s$) is from 0.7 to 1.2 at 25 degrees Celsius and a wavelength of 589 nm.

7. The cosmetic composition as claimed in claim 1 wherein the opacifying particles have a refractive index of at least 1.7 at 25 degrees Celsius and at a wavelength of 589 nm.

8. A method for improving one or more skin characteristics comprising the steps of:
   I. providing a composition as claimed in claim 1
   II. topically applying the composition to skin; and
   III. allowing the volatile liquid to evaporate from the particle active.

9. The cosmetic composition as claimed in claim 1 wherein the ratio of the refractive index of the core to the refractive index of the shell ($n_c/n_s$) is from 0.8 to 1.0 at 25 degrees Celsius and a wavelength of 589 nm.

10. The cosmetic composition as claimed in claim 1 wherein the opacifying particles have a refractive index from 2.0 to 2.7 at 25 degrees Celsius and at a wavelength of 589 nm.

* * * * *